United States Patent [19]

Chen

[11] Patent Number: 5,131,906
[45] Date of Patent: Jul. 21, 1992

[54] INCONTINENCE DEVICE

[76] Inventor: Fusen H. Chen, 12 Vernon La., Thompson, Conn. 06277

[21] Appl. No.: 583,239

[22] Filed: Sep. 17, 1990

Related U.S. Application Data

[63] Continuation-in-part of Ser. No. 260,401, Oct. 20, 1988, abandoned.

[51] Int. Cl.[5] .................................................. A61M 25/00
[52] U.S. Cl. .................................... 600/29; 606/198; 128/DIG. 25; 604/328; 604/104
[58] Field of Search ..................................... 600/29–32; 604/104–106, 327–329; 606/192, 198; 128/DIG. 25, 843

[56] References Cited

U.S. PATENT DOCUMENTS

| | | |
|---|---|---|
| 1,073,249 | 9/1913 | Kurtz et al. ........................ 604/105 |
| 1,878,671 | 9/1932 | Cantor . |
| 2,653,599 | 9/1953 | Bell . |
| 2,721,549 | 10/1955 | Ferraro . |
| 3,463,141 | 8/1969 | Mozolf . |
| 3,503,400 | 3/1970 | Osthagen et al. . |
| 3,642,004 | 2/1972 | Osthagen et al. . |
| 3,768,102 | 10/1973 | Kwan-Gett et al. . |
| 3,769,983 | 11/1973 | Merav ................................ 604/104 |
| 3,841,304 | 10/1974 | Jones . |
| 4,043,338 | 8/1977 | Homm et al. ...................... 604/105 |
| 4,349,029 | 9/1982 | Mott . |
| 4,457,299 | 7/1984 | Cornwell . |
| 4,710,169 | 12/1987 | Christopher . |
| 4,846,784 | 7/1989 | Haber ................................. 600/29 |
| 4,932,938 | 6/1990 | Goldberg et al. ................. 604/104 |
| 4,968,294 | 11/1990 | Salama .............................. 600/30 |

Primary Examiner—Stephen C. Pellegrino
Assistant Examiner—Ralph A. Lewis
Attorney, Agent, or Firm—Morris Kaplan

[57] ABSTRACT

Urethral blockage means for urinary incontinence has a centrally disposed member which may be either a solid rod or of a tubular configuration. A truncated spherical shell, fabricated of a flexible, resilient, silastic material of a predetermined stiffness and memory, depends from one end of the member. A plurality of elastic bands are uniformly spaced about and depend from the truncated end of said shell and connect to a centrally disposed, aperture-defining periphery of an insertion-limiting cap through which the member extends.

3 Claims, 3 Drawing Sheets

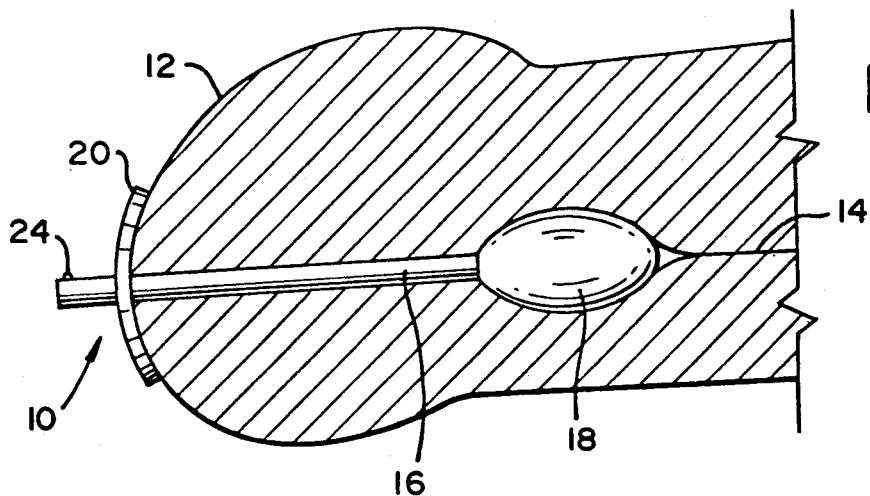
FIG. 1
FIG. 2　　FIG. 3　　FIG. 4
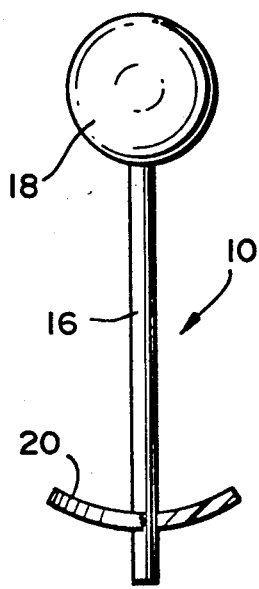 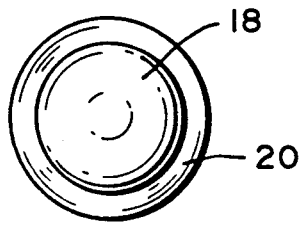 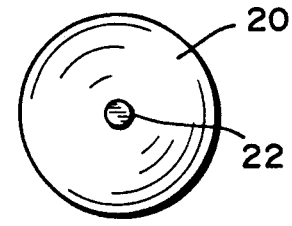
FIG. 5
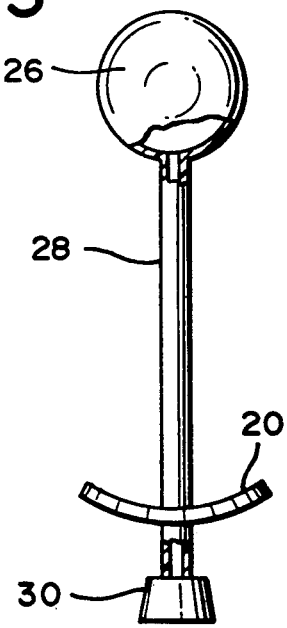
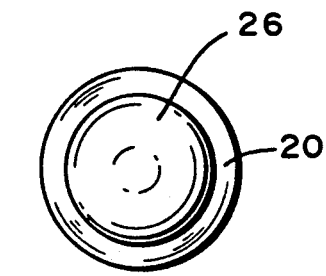 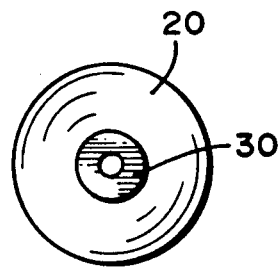
FIG. 6　　FIG. 7

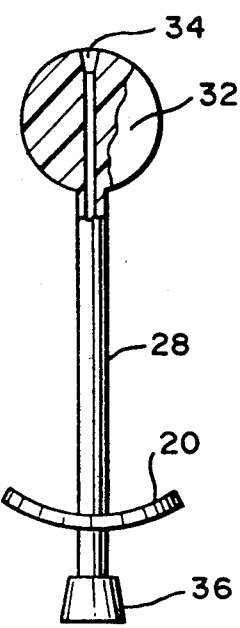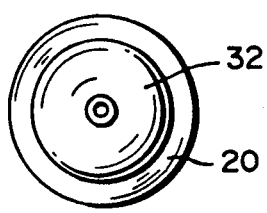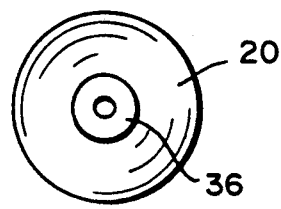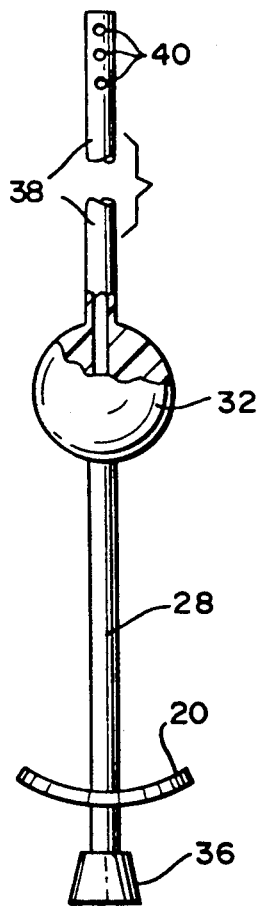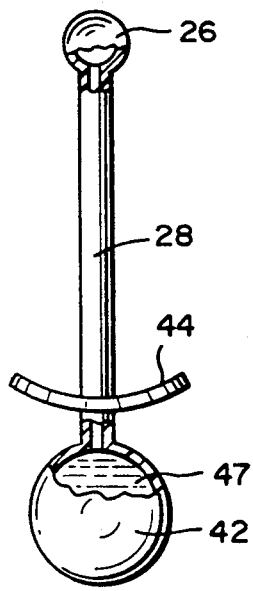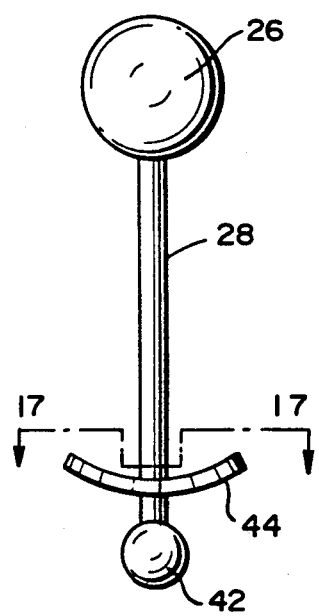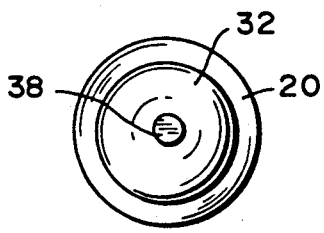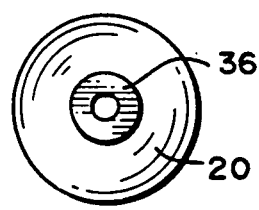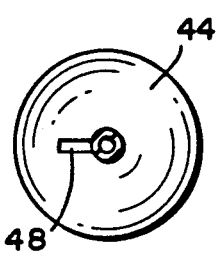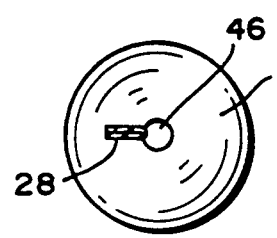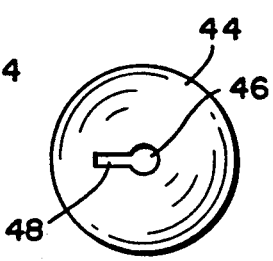

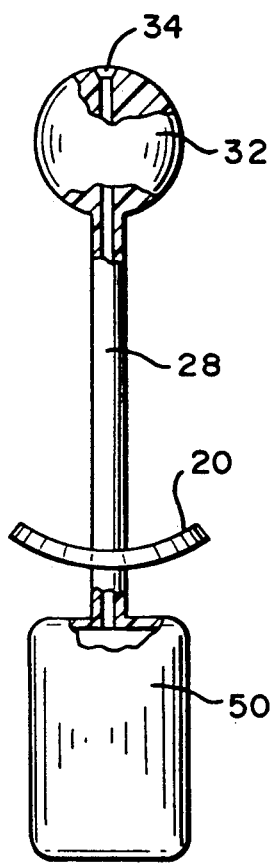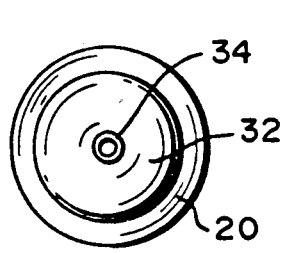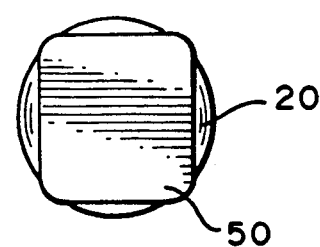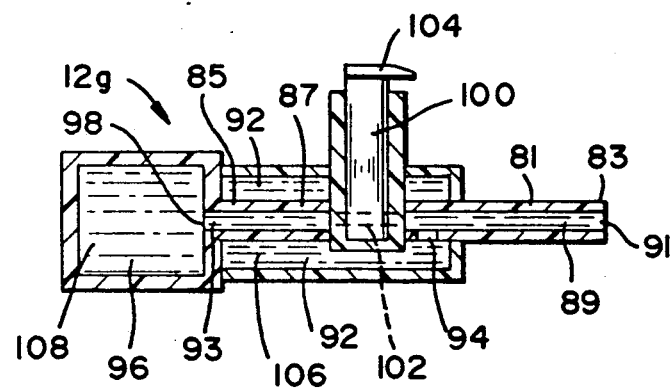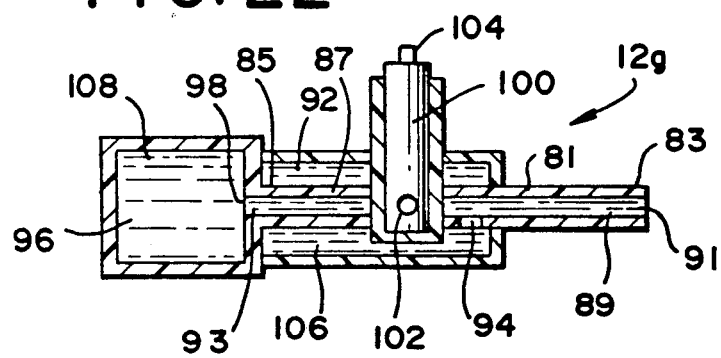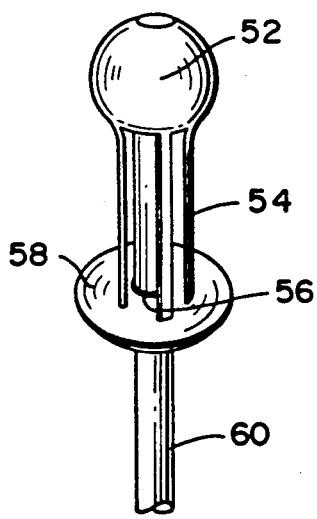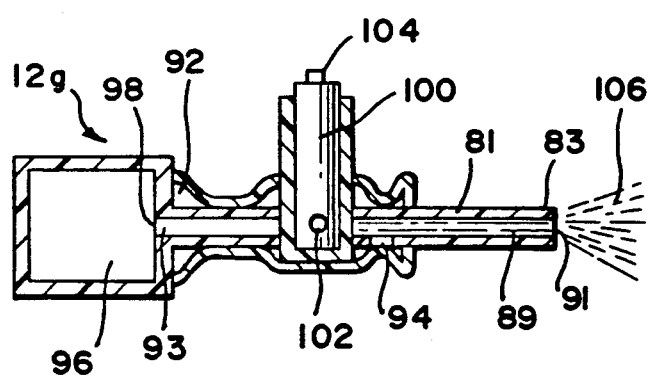

INCONTINENCE DEVICE

CROSS-REFERENCE TO RELATED APPLICATION

This application is a continuation-in-part of application Ser. No. 07/260,401, filed Oct. 20, 1988.

BACKGROUND OF THE INVENTION

The use of catheters for the treatment of urinary incontinence is well known. These devices are both bladder retained, as for instance the commonly used Foley type, and penially retained, as for instance U.S. Pat. Nos. 3,768,102 to Kwan-Gett; 4,457,299 to Christopher; and 4,457,299 to Cornwell.

These patents and other patent disclosures of the type are discussed in the above-identified parent application, the disclosure of which parent application is incorporated herein by reference.

These known devices are not fully satisfactory. Some of the problems encountered are:

the device, especially the bladder-retained type, may provide a direct rail for bacteria to access the bladder;

irritation and damage of the mucosae and underlying tissue;

device functionality relies upon sphincter muscle capability; and device requires especially trained or sophisticated handling.

SUMMARY OF THE INVENTION

The present invention is directed to a novel and improved device for controlling urinary incontinence that: is mechanically relatively simple and inexpensive to manufacture; does not require unique training or sophisticated handling to use; is frictionally retained in the urethral canal by an enlarged element that does not unduly enlarge the urethra and is located therein relatively far removed from the sphincter muscle and bladder; and may be either a simple blocking device or a drainage instrument.

For a more fully developed presentation of the invention, and preferred embodiments thereof, reference is made to the following descriptive matter, attached drawings, and claims.

BRIEF DESCRIPTION OF THE DRAWINGS

FIG. 1 is a side elevational view of a first embodiment of the invention, partly in section and penially inserted.

FIG. 2 is a side elevation of the device of FIG. 1 showing a depth of insertion limiting cap means partly in section and the device's bulbous retention means unstressed.

FIGS. 3 and 4 are respective top and bottom plan views of the device of FIG. 1.

FIG. 5 is a side elevational view, partly in section, of a second embodiment of the invention.

FIGS. 6 and 7 are respective top and bottom plan views of the device of FIG. 5.

FIG. 8 is a side elevational view, partly in section, of a third embodiment of the invention.

FIGS. 9 and 10 are respective top and bottom plan views of the device of FIG. 8.

FIG. 11 is a side elevational view, partly in section, of a fourth embodiment of the invention.

FIGS. 12 and 13 are respective top and bottom plan views of the device of FIG. 11.

FIG. 14 is a side elevational view, partly in section, of a fifth embodiment of the invention.

FIG. 15 is a view of the device of FIG. 14 after transfer of retention member distending fluid.

FIG. 16 is a plan view of the cap of FIG. 15.

FIG. 17 is a horizontal view taken on cut line XVII—XVII of FIG. 15 and shows the tubular element of the device disposed in the enlarged section of the cap's keyhole-shaped aperture.

FIG. 18 shows the tubular element of FIG. 17 closed by the slotted portion of the aperture.

FIG. 19 is a side elevational view, partly in section, of a sixth embodiment of the invention.

FIGS. 20 and 21 are respective top and bottom plan views of the device of FIG. 19.

FIGS. 22, 23, and 24 are side elevational views, partly in section, of a seventh embodiment of the invention and showing the valve member in different positions.

FIG. 25 is a perspective view of an eighth embodiment of the invention.

DETAILED DESCRIPTION OF THE INVENTION

Referring to the drawings which illustrate preferred embodiments of the invention and wherein like numerals indicate like elements of structure, there is shown in FIGS. 1 through 4 an incontinence device 10 disposed in the urethral canal 14 of a male member 12 whose parts, as well as those of the device, are not drawn to scale.

The device 10 has an elongated stem 16 that is generally uniformly circular in cross-section and a smooth surface, enlarged element 18 at its forward end. As shown, the device is of a relatively short length with respect to the canal and, in use, the enlargement is disposed relatively close to the canal entrance and substantially distant from the sphincter muscle and bladder to thereby not abet bacterial access beyond the device.

For clarity, the parts as illustrated are dimensionally exaggerated. In actuality, the stem is flexible and sufficiently slender so as not to unnecessarily distort the canal and the enlargement, which is preferably spherical when unstressed, is of a silastic material that is slightly deformable by the urethral canal structure and, in turn, is of a dimension to only slightly distend the canal wall whereby with minimal surface-to-surface contact effect a firm block to urinary passage, a continuous surface-to-surface contact to avoid pockets for potential bacterial growth and to further provide a hold against relative movement and consequent abrasion on the mucosa.

The materials of fabrication, as in all instant embodiments of invention, are, of course, inert and compatible with the human body and many be coated or otherwise treated to enhance inertness, passage in the canal and sterilization.

To limit insertion of the device into the canal, a flexible cap 20 is provided. The cap is configured to conform to the body portion external of the urethra and has an aperture 22 by which to be slidably, frictionally held on stem 16. The stem may optionally be provided with a nub element 24 at its free end whereby to inhibit accidental cap removal therefrom.

In place of aperture 22, a keyhole-shaped aperture may be provided; see FIGS. 16-18. The slot means of such keyhole shape provides a more positive positional lock of the cap on the stem to thus positively fix the device with respect to the urethra.

The second embodiment of the invention (FIGS. 5, 6, 7) is broadly somewhat similar to that described above but relies on an expandable head member 26, that may be a simple balloon. Member 26 is here shown expanded and in communication with tubular stem 28. The stem has a valve member 30, at its free end, wherethrough fluid is admitted to complete functional positioning of the device by expansion of head member 26.

The balloon-type member allows for deflation and thus facilitates device insertion and removal and provides a more readily conformability to the urethral canal encountered.

The third embodiment of the invention (FIGS. 8, 9, 10) differs from that of FIG. 5 in that the head member 32 for retention purposes functions as does that of enlargement 18 but has passage 34 therethrough that communicates with tubular stem 28 and valve means 36.

In this instance, the valve functions to permit drawing of urine or may be communicated to receptacle means for controlled voiding.

The fourth embodiment of the invention (FIGS. 11, 12, 13) is essentially that of FIG. 8 but additionally provides tubular means 38 that communicates with head passageway 34, is of a length to extend into the bladder and is perforated 40 at its bladder inserted part.

This fourth embodiment device is intended for the condition of organal urinary blockage, as at the prostate, the sphincter or at the bladder, and avoids device retention means located in or near the bladder or damaged parts.

The fifth embodiment of the invention (FIGS. 14, 15, 16, 17, 18) resembles that of FIG. 5, except that the valve means 30 has been replaced by a reservoir member 42 that communicates with stem 28 and the cap member 44 is of the keyhole-shaped aperture type.

In use, deflated member 26 is positioned in the urethral canal and, with the tubular stem 28, relatively slidably retained in enlarged aperture section 46, the reservoir is squeezed to transfer fluid 47 to expand head 26 to canal-retention configuration. Thereafter, cap 44 manipulated whereby to dispose stem 28 in slot section 48 of the keyhole configuration; said slot being of a dimension to fully collapse and lock onto stem 28 (FIG. 18).

The sixth embodiment of the invention (FIGS. 19, 20, 21) is useful for collecting urinary discharge and to this effect replaces valve 36 of the structure of FIG. 8 with receptacle 50.

FIGS. 22-24 show a seventh embodiment of the present invention. The embodiment 12g comprises a longitudinal body 81 having a distal end 83 which is adapted to be partially inserted through the urethral orifice, into the urethral canal, a proximal end 85, an intermediate section 87 and a bore 89 having an opening 91 at the distal end and an opening 93 at the proximal end. A first chamber 92 is secured about a portion of the intermediate section 87 of the longitudinal body 81 and includes an opening 94 which provides communication between the first chamber 92 and the bore 89 of the longitudinal body 81. A second chamber 96 is secured to the proximal end 85 of the longitudinal body and includes an opening 98 which is in fluid communication with the opening 93 at the proximal end 85 of the longitudinal body. A valve 100 is secured at the intermediate section 87 of the longitudinal body and controls the flow of fluid from the second chamber 96 into the bore 89 of the longitudinal body 81. A valve passageway 102 is selectively aligned with the opening 93 to allow communication between the second chamber and the bore 89. The passageway 102 is aligned in fluid communication with the second chamber 96 by means of a valve actuator 104. Referring to FIG. 22, the valve passageway 102 is in alignment to allow fluid communication between the second chamber and the longitudinal bore. FIG. 23 shows valve passageway 102 out of alignment with the opening 93, whereby fluid communication between the second chamber and the bore 89 is non-existent.

The embodiment 12g is designed to discharge a fluid 106, of the first chamber 92, into the bore 89 and then, upon exposure to the fluid 108 contained in the second chamber 96, cause the first fluid 106 to form a balloon-like member which is inflated by action of the fluid 108 and cause the distention of the walls of the urethral canal by the balloon-like member. The inflated balloon-like member prevents the voidance of fluids through the urethral canal. Preferably, the fluid 106 comprises a mixture of latex and silicone compound which, upon being discharged from the first chamber 92, the fluid 106 undergoes a curing reaction, so that upon exposure to the fluid 108, assumes a balloon-like formation. Preferably, the fluid 108 is a gas.

The eighth embodiment of the invention (FIG. 25) is adaptable to any of the stem or stem and valve or stem and reservoir means disclosed in FIGS. 2, 8, 11, and 19. In each of these instances of adaptation, the enlarged head for anchoring the device in the urethral canal and the insertion limiting cap means is replaced by an integral member comprised of a spherical shell 52 that is truncated at about one-third its lower section, is fabricated of a flexible, resilient silastic material that has a predetermined stiffness and memory whereby to substantially retain its spherical shape without unduly stressing the urethral canal structure. Depending from and uniformly spaced about the shell periphery at said truncated section are of a plurality of elastic bands 54 which at their opposite ends are uniformly spaced about or near, and affixed to, the centrally disposed aperture defining periphery 56 of a insertion limiting cap member 58.

As shown, the shell member is centrally affixed to the forward end of a stem element 60 that extends within the shell. The bands 54 are thus uniformly spaced about stem 60, which passes through the centrally disposed aperture 56 of cap 58.

Stem 60 may be either solid or tubular, as shown in FIGS. 8, 11, and 19, and in the latter instances, the tube pierces the shell and may be combined with either valvular means (FIGS. 8, 11) or a receptacle (FIG. 19) at its free end.

In use, a slight force is applied to the cap which thus stretches the bands and transmits to the shell to thereby dimensionally decrease the transverse extent of the shell and thus facilitate insertion of the shell and stem into a urethral canal. Upon achieving the desired extent of insertion, the force on the cap is released. Shell memory thereup induces the shell to assume its canal-retained configuration and the elastic bands draw the cap to its insertion limiting position.

The embodiments shown and described are only illustrative of the present invention and not to be construed as definitive thereof; since once apprised of the invention, changes in structure would be readily apparent to one skilled in the art. Hence, the present invention includes all modifications of structure encompassed within the spirit and scope of the following claims.

I claim:

1. A urinary incontinence device comprising:
   a flexible stem element;
   a truncated spherical shell centrally affixed at one end to one end of, and extending along, said stem;
   said shell truncation occurring at its other end, at a minor transverse diameter thereof and normal to the stem;
   said shell being fabricated of a silastic, flexible, resilient, elastic material;
   a plurality of elastic bands which are uniformly spaced about, and which each at one end depends from, the shell periphery at said truncation;
   said bands being at their opposite ends connected to a cap member;
   said cap member having a centrally disposed aperture through which said stem extends;
   the band to cap connections at said opposite band ends being uniformly spaced about an inner periphery of the cap that defines said aperture;
   said shell being adapted to decrease in dimension transverse to said stem when a tensile force is applied to said cap member to thereby stretch said bands along said stem;
   whereby to decrease the transverse dimension of said shell for facilitating insertion of said shell and associated portion of the stem into a urethral canal;
   said shell having a predetermined memory, softness, and dimension such that upon release of a said force, the shell substantially resumes its unstressed transverse configuration to anchor itself in said canal without unduly stressing the canal wall and said wall slightly decreasing the transverse extent of the shell;
   whereby to enhance surface-to-surface contact between the shell and canal wall to thus inhibit formation of pockets that may promote bacterial growth; and to enhance conformity between said contacting surfaces to thus inhibit relative movement therebetween; and
   said cap conforming to the external wall at the urethra entrance and adapted to inhibit further ingress of the shell and stem into the urethral canal.

2. A urinary incontinence device as in claim 1, wherein said stem is a solid element and said device functions as a urinary blocking member.

3. A urinary incontinence device as in claim 1, wherein:
   the stem element is tubular and the stem-to-shell connection at said one end of the stem is open to urinary flow when the device is inserted in a urethral canal, and
   valve means are disposed at the other end of the tubular stem for controlling such urinary flow.

* * * * *